United States Patent [19]

McKenna et al.

[11] Patent Number: 5,348,877
[45] Date of Patent: Sep. 20, 1994

[54] METHOD OF ADAPTING ANCHORAGE-DEPENDENT CELL LINES TO SUSPENSION CONDITIONS

[75] Inventors: Kevin A. McKenna, Spencer; Robert R. Granados, Ithaca, both of N.Y.

[73] Assignee: Boyce Thompson Institute for Plant Research, Inc., Ithaca, N.Y.

[21] Appl. No.: 29,274

[22] Filed: Mar. 12, 1993

[51] Int. Cl.$^5$ .................... C12N 5/00; C12N 5/02
[52] U.S. Cl. .................... 435/240.21; 435/240.25; 435/240.23; 435/240.2
[58] Field of Search ............ 435/252.2, 240.23, 240.2, 435/240.25

[56] References Cited

U.S. PATENT DOCUMENTS 5,024,947  6/1991  Inlow et al. .................... 435/240.31

OTHER PUBLICATIONS

Karlsson et al, Laboratory Investigation, 60(5): 659–666, (1989).
Oberlander et al, Archives of Insect Biochemistry and Physiology, 5(2): 81–89, (1987), Abstract.
Carroll, Ippolito, and DeWolf "Heparin-Binding Agglutinin on Human Teratocarcinoma Cells", Biochem. Biophys. Res. Commun., 1982, 109/4 (1353–1359).
Thurn and Underhill, Heparin-Induced Aggregation of Lymphoid Cells; J. Cell Physiol., 1986, 126/3 (352–358).
Gill, Silbert and Silbert, Effects of Heparin Sulfate Removal on Attachment and Reattachment of Fibroblasts and Endothelial Cells; Biochemistry, 1986, 25/2 (405–410).
Moore, Mahaffey, and Zboran, Heparin-Induced Agglutination of Erythrocytes in Horses; American Journal of Veterinary Research 48 (1). 1987: 68–71.
Mahaffey and Moore, Erythrocyte Agglutination Associated with Heparin Treatment in Three Horses J. American Veterinary Medical Association 1986. 189 (11): 1478–1480.
Kozlov, Kaznacheev, Lozovoi, and Lyakhovich, Mechanism of Action of Heparin of Lymphocytes in Vitro; Bull. Exp. Biol. Med., 1978, 84/11 (1612–1614).
Dougherty, et.al.—"Physical Factors That Affect In Vitro Autographica californica Nuclear Polyhedrosis Virus Infection" (Applied and Environmental Microbiology, May 1981, pp. 1166–1172).

Primary Examiner—Douglas W. Robinson
Assistant Examiner—Maria Luisa Osoteo
Attorney, Agent, or Firm—Barnard, Brown & Michaels

[57] ABSTRACT

Normally anchorage-dependent insect cell lines are adapted to replicate under suspension conditions by addition of heparin to the culture medium and selection for resulting suspension-tolerant cells.

14 Claims, No Drawings

METHOD OF ADAPTING ANCHORAGE-DEPENDENT CELL LINES TO SUSPENSION CONDITIONS

FIELD OF THE INVENTION

The invention pertains to the field of propagation of cell lines. More particularly, the invention pertains to methods of propagating cells in suspension.

BACKGROUND OF THE INVENTION

The past decade has witnessed the rapid emergence of genetic engineering technology coupled with major improvements in the development of large-scale insect cell culture processes. These developments have led to the widespread use of insect cells as a valuable host cell system for the expression of recombinant proteins.

One of the insect cell lines which has shown great promise is BTI-Tn-5B1-4, established at Boyce Thompson Institute, Ithaca, N.Y. and commercially available as High Five TM cells from Invitrogen Corp. The cell line is on deposit at the American Type Culture Collection as ATCC CRL 10859. This novel cell line is the subject of copending patent application Ser. No. 07/983,821, filed Dec. 1, 1992. These cells were derived from eggs of the Cabbage Looper (*Trichoplusia ni*). They have been found to be particularly susceptible to baculoviruses, which are adaptable to genetic modifications which lead to high levels of secretion of proteins.

Since this time, the BTI-Tn-5B1-4 cells have been maintained continuously as an anchorage dependent cell line, first in complete medium, and now in both complete and serum-free medium. By "anchorage dependent", we mean that the cell line forms layers and clumps attached to the vessel in which the cells are cultivated. The above-referenced copending application is directed to these cells in an anchorage-dependent form, as no means had been found at that time to adapt the cell line to grow in suspension.

Several research groups, inside and outside Boyce Thompson Institute, the assignee of this application and the above-referenced copending applications, have attempted to adapt this cell line to suspension conditions, i.e. maintenance of the cell line as individual cells suspended in a medium. All have met with the same result: severe clumping.

The anchorage dependency of the cells presents no problem for research, but limits the applicability of the cell line for commercial applications where in order to scale up the production it is desirable to maintain the cell lines in bioreactors (i.e., in suspension).

It will be understood by those skilled in the art that the problem of clumping or anchorage-dependency is not limited to the BTI-Tn-5B1-4 cell line, but is common to many cell lines.

Heparin is "an acid mucopolysaccharide acting as an antithrombin, antithromboplastin, and antiplatelet factor to prolong the clotting time of whole blood. It occurs in a variety of tissues, most abundantly in liver." (McGraw-Hill *Dictionary of Scientific and Technical Terms*, 1978, p.741)

Heparin acts as an anticoagulant by increasing the rate of formation of irreversible complexes between antithrombin III and the serine protease clotting factors. (Lubert Stryer, *Biochemistry*, 1988, p.255)

Although heparin is a known anticoagulant for blood cells, as shown by the above references, its effect upon cell lines is less clear. It will be noted that the following references all deal with human or mammalian cell lines, or with blood. We are aware of no prior art which deals with the effect of heparin upon insect cells.

Carroll, Ippolito, and DeWolf (Div. Cell. Genet., Charles A. Dana Res. Inst., Beth Israel Hosp., Boston) reported that human teratocarcinoma (HT) cell line HT-D (1218E) formed 40–60% rosettes which was inhibited by addition of heparin to the cell suspensions. ... Heparin was capable of disrupting monolayer formation by cell line HT-D (1218E) when added to cultured cells growing in vitro. These results suggest that a heparin, or more likely, heparan sulfate-binding component on the surface of some human teratocarcinoma cell lines may be involved in cellular adhesion.-"—HEPARIN-BINDING AGGLUTININ ON HUMAN TERATOCARCINOMA CELLS; *BIOCHEM. BIOPHYS. RES. COMMUN.*, 1982, 109/4 (1353–1359)

Note: "Heparan Sulfate is like heparin except it has fewer N- and O-Sulfate groups and more N-acetyl groups", Stryer Biochemistry, 1988, p 276. For the purposes of this disclosure, heparin and heparan sulfate are considered equivalent and will be referred to generically as "heparin".

The above reference would seem to teach that heparin inhibits aggregation. However, the following references would indicate exactly the opposite: that heparin *induces* aggregation of cells.

Thurn and Underhill (Department of Anatomy, School of Medicine and Dentistry, Georgetown University, Washington, D.C.) reported that "The effects of different carbohydrates on cell-to-cell adhesion were examined in an aggregation assay, which consisted of swirling a suspension of cells and monitoring the loss of single cells with a Coulter Counter. Of the carbohydrates tested, only heparin and dextran sulfate induced cell aggregation. This effect occurred in freshly isolated mouse splenocytes and in cultured cells of lymphoid origin (P388, YAA-Cl) but not in cell lines of fibroblastic origins (3T3, SV-3T3, BHK, and PY-BHK). Using the YAA-Cl cell line for further study, *we found that aggregation could be induced by relatively small amounts of heparin* (<10 μg/ml)." (emphasis added)—HEPARIN-INDUCED AGGREGATION OF LYMPHOID CELLS; *J. CELL. PHYSIOL.*, 1986, 126/3 (352–358)

Gill, Silbert and Silbert (Department of Medicine, Harvard Medical School, Boston, Mass.) reported the following experiments: "Human skin fibroblasts and calf aorta endothelial cells were grown as tissue culture monolayers in the presence of (sup 3sup 5S) sulfate in order to label the glycosaminoglycan portions of proteoglycans for investigation of their role in cell attachment. The (sup 3sup 5S) glycosaminoglycans were then selectively removed from the cell monolayers by the addition of various glycosaminoglycan-degrading enzymes. As previously described, in contrast to trypsin treatment none of these enzymes removed any cells from the culture plates. Incubation with a preparation from Flavobacterium heparinum left only small stubs of (sup 3sup 5S) glycosaminoglycans on the cell monolayers, indicating that all the cell-surface proteoheparan (sup 3sup 5S) sulfate and proteochondroitin (sup 3sup 5S) sulfate was accessible to this enzyme preparation. The treatment did not change the amount or time of incubation with trypsin necessary for release of the cells from the monolayers. Thus, cell attachment was not weakened by removal of heparan sulfate or chondroitin sulfate. In contrast, neither fibroblasts nor endothelial cells in suspension would reattach in the presence of the F. heparinum preparation while reattachment occurred readily in the presence of chondroitin ABC lyase. This provides evidence that heparan sulfate, but not chondroitin sulfate, is involved in the process of cell attachment even though neither is necessary for maintaining attachment."—EFFECTS OF HEPARAN SULFATE REMOVAL ON ATTACHMENT AND REATTACHMENT OF FIBROBLASTS AND ENDOTHELIAL CELLS; *BIOCHEMISTRY*, 1986, 25/2 (405–410)

See also: Moore, Mahaffey, and Zboran (Dep. Of Large Animal Med. And Physiol.-pharmacol., Coil. Of Vet. Med., Univ. Of Ga., Athens, Ga.), HEPARIN-INDUCED AGGLUTINATION OF ERYTHROCYTES IN HORSES; *American Journal of Veterinary Research* 48 (1). 1987; and Mahaffey and Moore (Dep. Vet. Path., Coll. Vet. Med., Univ., Athens, Ga.), ERYTHROCYTE AGGLUTINATION ASSOCIATED WITH HEPARIN TREATMENT IN THREE HORSES *J. American Veterinary Medical Association* 1986. 189 (11):1478–1480 (10 ref.) (Note: "Erythrocytes" are also known as "red blood cells").

Since the primary reason for experimentation with the insect cell lines which led to the invention is the production of various substances through genetic engineering, it was considered important that heparin not interfere with this process. The following reference would appear to teach away from the use of heparin in this application:

"In experiments on CBA mice in which a 2% suspension of red blood cells was used as the *antigen, heparin substantially prevented the migration of antibodies from antibody-producing cells in vitro.* . . . It is concluded that heparin is able to interact with the outer membrane of immunocompetent cells and to inhibit migration of antibodies synthesized by them into the surrounding medium."—Kozlov, Kaznacheev, Lozovoi, and Lyakhovich (Lab. Clin. Immunopathol., Inst. Clin. Exp. Med., Siberian Branch, Acad. Med. Sci. USSR), MECHANISM OF ACTION OF HEPARIN OF LYMPHOCYTES IN VITRO; BULL. EXP. BIOL. MED., 1978, 84/11 (1612–1614)

Dougherty, et. al. discussed the effect of heparin, among other substances, on enhancing virus absorption by insect cell lines in an article entitled "Physical Factors That Affect In Vitro Autographica californica Nuclear Polyhedrosis Virus Infection" (Applied and Environmental Microbiology, May 1981, pp. 1166–1172). The reference does not discuss the effect of heparin on cell propagation or attachment. The cells were not passaged serially in the presence of heparin, nor was selection for non-attachment dependent cells performed.

SUMMARY OF THE INVENTION

Insect cells have been adapted to suspension culture by the addition of heparin, a proteoglycan with anticoagulation properties. Additional passages of the cell culture are selected from cells which are in suspension after the heparin treatment, resulting in a viable cell line which may be successfully maintained in suspension.

The heparin treatment does not affect the ability of the cells to be infected by baculoviruses, nor does it appear to prevent the secretion of proteins.

DESCRIPTION OF THE PREFERRED EMBODIMENT

The preferred embodiment of the invention presents a method of adapting anchorage-dependent insect cell lines to propagation and growth under suspension conditions.

As will be seen in the examples below, the method comprises the addition of heparin to the cultivation medium. The heparin used was obtained from porcine intestinal mucosa, and was purchased from Sigma Chemical Company, St. Louis, Mo., although other suppliers and sources of heparin may be used within the teachings of the invention.

This heparin treatment has proven effective and non-toxic to the several cell lines tested at levels ranging from 100 Units/ml to 2,000 Units/ml. No tests were performed outside of this range, but we have no reason to believe the range to be critical in any way. We have standardized on a level of 100 Units/ml for our experimental use, but other levels of heparin would be effective within the teachings of the invention.

In initial tests with high-passage cells derived from the eggs of the Cabbage Looper *Trichoplusia ni* (Cell line BTI-Tn-5B1-4 commercially available as High Five TM cells from Invitrogen Corp.) the cells immediately adapted to suspension upon introduction of heparin to the medium. These cells had been selected over the passages from the least anchorage-dependent cells from the original stock (test described below as Example 1).

When the cells were not pre-selected or were more anchorage-dependent it was necessary to select those cells in suspension after each passage with heparin. Within a few passages, the cell line was entirely suspension adapted. Example 2, below, is the same BTI-Tn-5B1-4 cell line, but from an earlier passage before the selection for lower anchorage dependency. Example 3, below, uses another cell line which was not preselected to any extent.

While this specification and the examples below discuss the invention in terms of BTI-Tn-5B1-4 and one other cell line, it will be understood that the teachings of the disclosure are not limited to those cell lines, which were chosen because the inventor herein was working with them already, not for any specific applicability of the method to those lines.

INSECT SUSPENSION CELL CULTURE EXAMPLES

Example 1

BTI-Tn-5B1-4 cells in EXCELL-400 Serum-Free Medium

BTI-Tn-5B1-4 (*Trichoplusia ni* egg cell line) cells at passage #149, were incubated with various concentrations of heparin (2,000, 1,000, and 500 Units/ml) for 2 days at 28° C. in individual wells of a 24-well tissue culture plate. Since no obvious toxic effects were observed in the cells due to heparin, the cells were combined and transferred to a 25 ml spinner flask containing 20 ml fresh EXCELL-400 medium (total volume $\approx$23 ml). The final concentration of heparin at this point was $\approx$800 Units/ml. After 24 hours, cell density appeared high, at this point the 2nd passage was established at a split ratio of 3 ml cell suspension to 20 ml fresh medium. Spin rate and incubation temperature were maintained at $\approx$90 RPM and 28° C. respectively.

Cellular growth rate decreased following the 2nd passage. Cellular morphology was determined to be predominantly round with single or double cell combinations also predominating. Small clumps were noted but were few in number. Heparin concentration was ≈200 Units/ml at this stage. By the fourth passage, cell growth had increased. Cell densities were estimated to be $2-3 \times 10^6$ cells/ml.

In order to confirm the effect of the heparin in the medium, a second spinner flask containing the same concentration of cells but without heparin was prepared at passage four. This culture was passaged twice, after which time it was discontinued due to severe clumping. The control flask containing heparin was also passaged at the same time and in the same manner and showed no evidence of clumping.

At passage seven, heparin concentration was reduced to 100 Units/ml and new cultures were set up using larger 50 ml spinner flasks interchangeably with 25 ml flasks. Subculture (i.e. passaging) routines were on 3 and 4 day cycles. At passage 13, a trial recombinant viral infection was performed utilizing a glycosylated mammalian protein, secreted alkaline phosphatase (SEAP), over a seven day period. Although expression of this protein was low during this experiment (Table 1.), it is believed that under optimal conditions, such as seen during stationary culture testing, expression could be increased. To date, suspension BTI-Tn-5B1-4 cells have been passaged over seventy times in EXCELL-400 medium with heparin concentrations as low as 50 Units/ml.

TABLE 1

SEAP expression in BTI-Tn-5B1-4 cells in suspension culture.
Secreted Alkaline Phosphatase (SEAP)

| Day | Activity Units/ml | Activity Units/$10^6$ cells | % Secretion |
|---|---|---|---|
| 1 | 0.14 | 0.60 | 82.7 |
| 2 | 0.61 | 1.50 | 81.0 |
| 3 | 1.96 | 2.45 | 88.6 |
| 4 | 2.89 | 2.22 | 89.2 |
| 5 | 3.14 | 1.96 | 89.1 |
| 6 | 3.87 | 3.22 | 100.0 |
| 7 | 3.58 | 3.98 | 95.2 |

Example 2

BTI-Tn-5B1-4 cells in EXCELL-400 Serum-Free Medium (2nd culture)

A second suspension culture of BTI-Tn-5B1-4 cells in EXCELL-400 medium with 100 Units heparin/ml, was established from a stationary (i.e., anchorage-dependent) stock of BTI-Tn-5B1-4 cells that had been frozen in liquid nitrogen for over one year. These cells were frozen at passage 78, revived, and passaged another ten times before attempting to adapt them to suspension conditions. At passage #88, a four day old stationary culture of BTI-Tn-5B1-4 cells was shaken from the flask, and transferred (≈5 ml) directly to a 25 ml spinner flask containing 15 ml fresh medium and 100 Units heparin/ml. Significant clumping occurred within 24 hours, At this point, the larger clumps were allowed to settle (≈5 min) prior to passaging. Gradually, utilizing heparin and the selection of non-clumped cells via a settling period, a suspension culture was established resembling the culture derived in example 1, above. Spin rate and incubation temperature were maintained at ≈90 RPM and 28° C., respectively. Afterward, these cells have been passaged 21 times in EXCELL-400 medium with 100 Units heparin/ml, and have remained in suspension.

Example 3

Tn-FB cells in EXCELL-400 Serum-Free Medium

The method of the invention was tested on a different cell line which normally grows in attached monolayers. A suspension culture of Tn-FB (*Trichoplusia ni*—Fat Body) cells (passage #75) was set up in the same manner as that described for the second BTI-Tn-5B1-4 suspension culture (Example 2 above). This cell line also clumped rapidly in the first four passages. By passage #5, these cells appeared predominantly "teardrop or tadpole" shaped, and were mostly in single or smaller clumps of 3-4 cells. By passage #10, these cells looked very healthy and were predominantly singular. Spin rate and incubation temperature were maintained at ≈90 RPM and 28° C., respectively. To date, these cells have been passaged 21 times in EXCELL-400 medium with 100 Units heparin/ml.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

I claim:

1. The method of establishing a suspended cell line from an anchorage-dependent insect cell line comprising the steps of:
   a) providing a culture of normally anchorage-dependent cells in a culture medium,
   b) adding heparin to the culture medium of said anchorage dependent cell line,
   c) selecting the cells which are in suspension after the addition of heparin,
   d) subculturing the cells which were selected in step c) to a fresh culture medium containing heparin,
   e) repeating steps c) and d) until a suspended cell line is established.

2. The method of claim 1 in which the anchorage-dependent insect cell line is derived from the Cabbage Looper, *Trichoplusia ni.*

3. The method of claim 2 in which the anchorage-dependent insect cell line is BTI-Tn-5B1-4, ATCC CRL 10859.

4. The method of claim 2 in which the anchorage-dependent insect cell line is derived from the fat bodies of the Cabbage Looper, *Trichoplusia ni.*

5. The method of claim 1 in which the heparin added to the culture medium in step b) of claim 1 is in a concentration of 50 units/ml to 2,000 units/ml.

6. The method of claim 1 in which the culture medium of step d) of claim 1 is serum free.

7. The method of claim 1 in which the heparin contained in the culture medium of step d) of claim 1 is in a concentration of 50 units/ml to 2,000 units/ml.

8. A culture of insect cells in suspension wherein the culture medium contains heparin, produced by the steps of:
   a) providing a culture of normally anchorage-dependent cells in a culture medium,
   b) adding heparin to the culture medium of said anchorage dependent cell line,
   c) selecting the cells which are in suspension after the addition of heparin, d) subculturing the cells which were selected in step c) to a fresh culture medium containing heparin, e) repeating steps c) and d) until a suspended cell line is established.

9. The culture of claim 8 in which the anchorage dependent insect cell line is derived from the Cabbage Looper, *Trichoplusia ni.*

10. The culture of claim 9 in which the anchorage dependent insect cell line is BTI-Tn-5B1-4, ATCC CRL 10859.

11. The culture of claim 9 in which the anchorage dependent insect cell line is derived from the fat bodies of the Cabbage Looper, *Trichoplusia ni.*

12. The culture of claim 8 in which the heparin added to the culture medium in step b) of claim 8 is in a concentration of 50 units/ml to 2,000 units/ml.

13. The culture of claim 8 in which the culture medium of step d) of claim 8 is serum free.

14. The culture of claim 8 in which the heparin contained in the culture medium of step d) of claim 8 is in a concentration of 50 units/ml to 2,000 units/ml.

* * * * *